US008142618B2

(12) United States Patent
Hugo et al.

(10) Patent No.: US 8,142,618 B2
(45) Date of Patent: Mar. 27, 2012

(54) PROCESSES FOR PREPARING PURE XYLYLENEDIAMINE

(75) Inventors: Randolf Hugo, Dirmstein (DE); Kirsten Dahmen, Mannheim (DE); Sabine Huber, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 887 days.

(21) Appl. No.: 12/278,080

(22) PCT Filed: Jan. 24, 2007

(86) PCT No.: PCT/EP2007/050679
§ 371 (c)(1),
(2), (4) Date: Aug. 1, 2008

(87) PCT Pub. No.: WO2007/088131
PCT Pub. Date: Aug. 9, 2007

(65) Prior Publication Data
US 2009/0020407 A1    Jan. 22, 2009

(30) Foreign Application Priority Data

Feb. 1, 2006    (EP) .................................. 06101145

(51) Int. Cl.
*B01D 3/10* (2006.01)
(52) U.S. Cl. .................................. 203/94; 203/DIG. 19
(58) Field of Classification Search ............ 203/94, 203/DIG. 19; 564/305, 424
See application file for complete search history.

(56) References Cited

U.S. PATENT DOCUMENTS

| | | | |
|---|---|---|---|
| 3,647,054 A * | 3/1972 | Tsuboi et al. ............ 203/29 |
| 4,482,741 A | 11/1984 | Kurek | |
| 6,359,177 B1 * | 3/2002 | Brady et al. ............ 564/424 |
| 6,547,933 B2 * | 4/2003 | Marion et al. ............ 203/78 |
| 6,646,163 B2 * | 11/2003 | Nakamura et al. ....... 564/388 |
| 7,307,190 B2 * | 12/2007 | Pennemann et al. ...... 564/347 |
| 7,323,597 B2 | 1/2008 | Hugo et al. | |
| 7,323,598 B2 | 1/2008 | Hugo et al. | |
| 7,339,080 B2 | 3/2008 | Hugo et al. | |
| 2007/0010693 A1 | 1/2007 | Hugo et al. | |
| 2007/0088179 A1 | 4/2007 | Hugo et al. | |
| 2008/0091049 A1 | 4/2008 | Hugo et al. | |
| 2008/0154061 A1 | 6/2008 | Ernst et al. | |
| 2008/0161609 A1 | 7/2008 | Hugo et al. | |

FOREIGN PATENT DOCUMENTS

| | | |
|---|---|---|
| DE | 102005003315 | 8/2006 |
| DE | 102005008929 | 8/2006 |
| DE | 102005036222 | 2/2007 |
| DE | 102005045806 | 3/2007 |
| EP | 1193244 | 4/2002 |
| EP | 1193247 | 4/2002 |
| EP | 1279661 | 1/2003 |
| JP | 2002-88032 | 3/2002 |

(Continued)

*Primary Examiner* — Duane Smith
*Assistant Examiner* — Patrick McCarty
(74) *Attorney, Agent, or Firm* — Connolly Bove Lodge & Hutz LLP

(57) ABSTRACT

A process comprising: continuously distilling a crude xylylenediamine in a column to form a pure xylylenediamine and a bottom product, wherein the column comprises a distillation column having a side draw and the distillation column is operated under a reduced pressure and a bottom temperature of 185° C. or less; drawing off the pure xylylenediamine from the side draw; evaporatively concentrating the bottom product of the distillation column in an additional evaporation stage to form a condensate; and returning the condensate into the distillation column.

17 Claims, 2 Drawing Sheets

FOREIGN PATENT DOCUMENTS

| | | |
|---|---|---|
| JP | 2003-26638 | 1/2003 |
| SU | 322322 | 11/1971 |
| WO | WO-2005/026098 | 3/2005 |
| WO | WO-2005/026099 | 3/2005 |
| WO | WO-2005/026100 | 3/2005 |
| WO | WO-2005/026101 | 3/2005 |
| WO | WO-2005/026102 | 3/2005 |
| WO | WO-2005/026103 | 3/2005 |
| WO | WO-2005/026104 | 3/2005 |
| WO | WO-2005/028417 | 3/2005 |

* cited by examiner

PROCESSES FOR PREPARING PURE XYLYLENEDIAMINE

CROSS-REFERENCE TO RELATED APPLICATIONS

This application is a national stage application, under 35 U.S.C. §371, of PCT/EP2007/050679, filed Jan. 24, 2007, which claims priority of European Patent Application No. 06101145.8, filed Feb. 1, 2006.

BACKGROUND OF THE INVENTION

Xylylenediamine (bis(aminomethyl)benzene) is a useful starting material, for example for the synthesis of polyamides, epoxy hardeners or as an intermediate for preparing isocyanates.

The expression "xylylenediamine" (XDA) comprises the three isomers ortho-xylylenediamine, meta-xylylenediamine (MXDA) and para-xylylenediamine.

Crude xylylenediamine can be prepared, for example, by ammoxidizing xylene and subsequently hydrogenating the resulting phthalonitrile. Possible preparation processes are described, for example, in the applications mentioned below.

U.S. Pat. No. 4,482,741 (UOP Inc.) describes the hydrogenation of phthalonitrile (PN) in the presence of ammonia, a specific catalyst and XDA as a solvent.

EP-A2-1 193 247 and EP-A1-1 279 661 (both Mitsubishi Gas Chem. Comp.) respectively relate to a process for purifying isophthalonitrile (IPN) and to a process for preparing pure XDA.

EP-A2-1 193 244 (Mitsubishi Gas Chem. Comp.) describes a process for preparing XDA by hydrogenating phthalonitrile which is synthesized in a preceding stage by ammoxidation of xylene, the vaporous product of the ammoxidation stage being contacted directly with a liquid organic solvent (quench) and the resulting quench solution or suspension being fed to the hydrogenation.

The purification of the crude XDA obtained is also described in the following patent applications:

JP 2002-088032 (Mitsubishi Gas Chem. Co, Inc.) describes a method for purifying XDA by feeding an inert gas to a condenser, the column top pressure being kept at 53 mbar or lower and the outlet temperature of the condenser being kept at 110° C. or lower. The inert gas strips out components which have a lower boiling point than XDA, so that they are not condensed completely, if at all, but rather are drawn off via the top with the inert gas. A high condensation temperature promotes the effect. However, the burden on the vacuum machine is increased by the inert gas and the components stripped can be condensed out of the inert gas only with difficulty, so that what remains is essentially incineration in a muffle or flare. According to claim 2, inert gas is added as in claim 1 and the bottom temperature is restricted to 180° C. This either gives rise to a large product loss via the bottom or requires a very low vacuum, which, though, is difficult and complicated to generate owing to the inert gas addition.

U.S. Pat. No. 3,647,054 (Japan Gas Chemical) describes the purification of the crude xylylenediamine by adding an alkaline component and subsequent heating in order to hydrolyze residues of unhydrogenated or incompletely hydrogenated phthalonitrile or cyanobenzylamine to subsequently obtain pure xylylenediamine by distillation. Otherwise, phthalonitrile and cyanobenzylamine can barely be separated from xylylenediamine by distillation. The conditions for the hydrolysis reaction are described. Regarding the purifying distillation, the examples mention merely that operation is effected at reduced pressure. U.S. Pat. No. 3,647,054 does not discuss dissociation or decomposition products which are formed at relatively high temperature from xylylenediamine in the distillation and contaminate the product.

SU-A-322 322 of Jan. 26, 1968 (Galperin et al.) describes the purification of crude xylylenediamine which comprises nitrites as secondary components by hydrolyzing the secondary components at 200° C. in the presence of alkali or ammonia. The purifying distillation is not described in detail. There is no discussion of the problems of product decomposition or elimination of ammonia at relatively high temperature.

JP-B-700 14 777 (Japan Gas Chem. Co) describes the purification of xylylenediamine by adding from 0.5 to 5% by weight of an alkaline substance to the crude xylylenediamine based on unreacted phthalonitrile. The crude xylylenediamine was obtained by hydrogenating phthalonitrile in a homogeneous liquid phase of liquid ammonia and organic solvent. Subsequently, the mixture is distilled.

JP-A-2003 026638 (Mitsubishi Gas Chem. Co, Inc.) describes a complicated extraction process with water and aromatic or saturated hydrocarbons for XDA purification. To this end, phthalonitrile is prepared by ammoxidizing xylene, and the reaction gas is quenched with solvent, admixed with ammonia and hydrogenated. Once ammonia and solvent have been removed, crude xylylenediamine is obtained. Water and at least one aromatic or saturated solvent are added. After phase separation, pure xylylenediamine is obtained with the aqueous phase, from which pure xylylenediamine is obtained by distillation.

In order to obtain pure XDA, some of the abovementioned purifications describe complicated processes with which XDA is, for example, purified by extraction, or assistants are added which are intended to ensure the required high purity of the XDA. The addition of assistants is intended to result in hydrolysis of corresponding nitrile which is still present as an impurity in the crude xylylenediamine after the hydrogenation as a result of incomplete reaction.

The processes described are complex in apparatus terms and as a result of the handling of large solvent streams and/or additional components.

The two German patent applications 102005003315.6 of Jan. 24, 2005 and 102005008929.1 of Feb. 24, 2005 (both BASF AG) relate to low-pressure PN hydrogenation in the presence of Raney catalysts.

WO-A-05/028417, WO-A-05/026102, WO-A-05/026103, WO-A-05/026104, WO-A-05/026100, WO-A-05/026101, WO-A-05/026098, WO-A-05/026099 and the two German patent applications 102005036222.2 of Aug. 2, 2005 and 102005045806.8 of Sep. 24, 2005 (all BASF AG) each relate to processes for preparing XDA. All of these processes afford crude xylylenediamine which subsequently has to be purified further.

For example, WO-A-05/028417 teaches on page 8 that the removal of relatively low-and relatively high-boiling by-products can also be effected in a side draw column or dividing wall column, in which case pure xylylenediamine is obtained via a liquid or gaseous side draw. Owing to reactions in the distillation bottoms of crude XDA at high temperatures, it is possible in this way to obtain XDA in good yield only when the distillation is effected at very low pressure in order to restrict the bottom temperature. This is relatively complicated in apparatus terms. In order to obtain pure XDA in the side draw, a product loss via the bottom has to be accepted in the case of vacuum which is easier to realize on the industrial scale. When the yield is increased, the rising bottom temperature leads to product decomposition, in which case the decomposition products, for example methylbenzylamine, contaminate the XDA withdrawn in the side draw. It is thus possible either to obtain pure XDA with a relatively low yield or contaminated XDA with a higher yield.

BRIEF SUMMARY OF THE INVENTION

The present invention relates to a process for preparing a pure xylylenediamine (XDA) by continuously distilling crude xylylenediamine in a column.

It was an object of the present invention to discover an improved, economically viable process for distillatively purifying crude xylylenediamine, especially meta-xylylenediamine (MXDA), in which xylylenediamine can be obtained in high purity and simultaneously in high yield.

In this document, what is meant by crude xylylenediamine is especially the reaction effluent from the hydrogenation of the corresponding phthalonitrile (PN), from which, if appropriate, ammonia has been removed fully or substantially and any solvent used in the hydrogenation has been removed fully or substantially, and which still comprises relatively high-boiling impurities and relatively low-boiling components, if appropriate also including a solvent.

One problem in the distillative purification of XDA is that product decomposition releases ammonia and/or low-boiling components, for example methylbenzylamine, which contaminate the product.

It has been shown experimentally that, surprisingly, pure xylylenediamine can be obtained by distillation of pure xylylenediamine, the xylylenediamine being obtained as a side draw stream by means of a side draw column and the distillation being performed at vacuum which is technically simple to realize.

Accordingly, a process has been found for preparing pure xylylenediamine (XDA) by continuously distilling crude xylylenediamine in a column, which comprises using a distillation column with side draw and drawing off the XDA in the side draw and evaporatively concentrating the bottom product of the distillation column in an additional evaporation stage and returning the condensate of this evaporation stage into the distillation column with side draw.

In the process according to the invention, additional process steps, for example extraction steps, are not absolutely necessary.

DETAILED DESCRIPTION OF THE INVENTION

Figure 1:
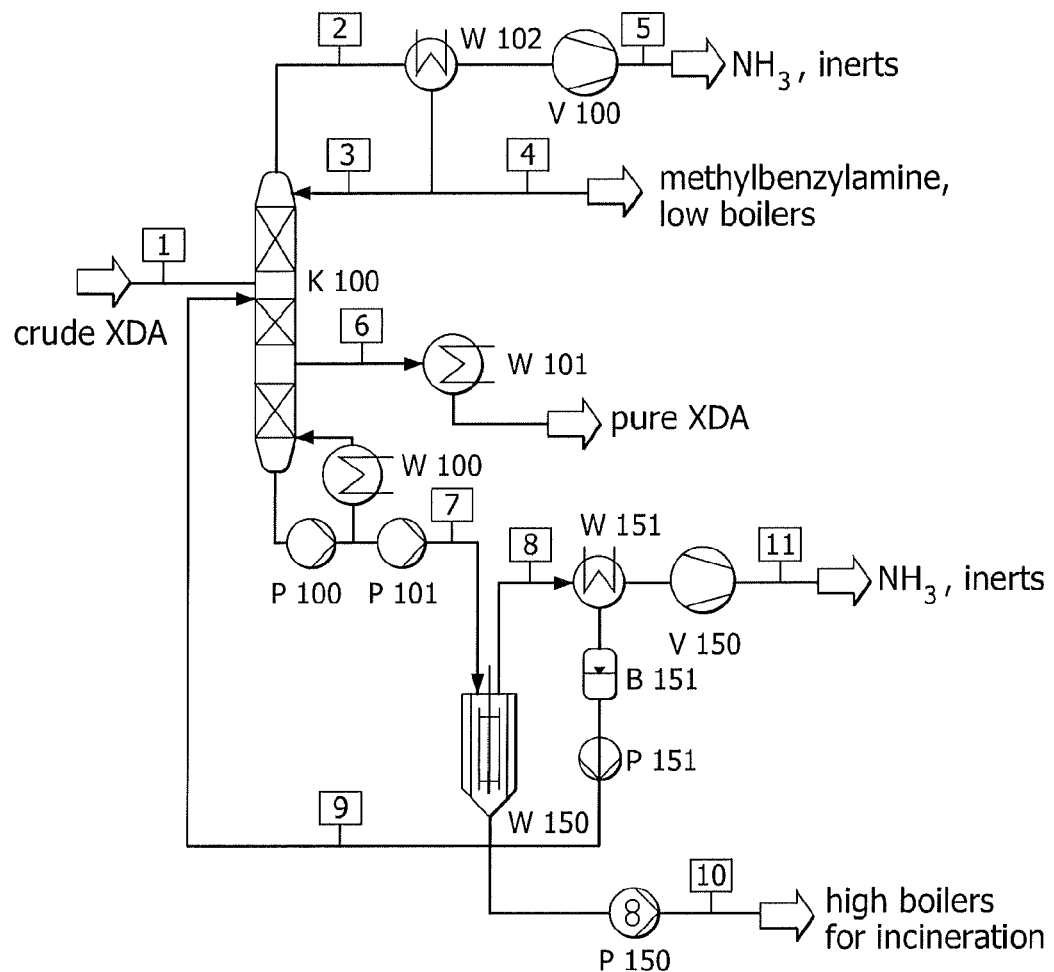
FIG. 1 is a schematic representation of a process in accordance with one embodiment of the present invention.

In a preferred embodiment, it is possible to dispense with the addition of assistants [for example KOH, NaOH, sodium phthalimide or potassium phthalimide or other alkaline components (bases), in each case in pure form or as a solution, and also reducing components such as $NaBH_4$ or $LiAlH_4$, and combinations of a base with a reducing component, and $H_3PO_3$], when they have not been used to hydrolyze incompletely hydrogenated nitrites. The addition of assistants to hydrolyze nitrites (for example phthalonitrile or cyanobenzylamine) may be useful in the event of incomplete reaction in the preceding hydrogenation stage. In the case that the crude product is sufficiently free of nitrile, the decomposition of the amine described in the present invention and the substantial suppression of decomposition and the recovery of pure XDA in good yield is not dependent upon additions of assistants according to the prior art outlined above.

For example, the distillation of meta-xylylenediamine releases ammonia and meta-methylbenzylamine which has a lower boiling point than meta-xylylenediamine. The distillation constantly forms new low boilers which appear as impurities in the distilled xylylenediamine. Limiting the bottom temperature in the distillation, for example to $\leq 185°$ C., in particular to $\leq 180°$ C., for example to a temperature in the range from 160 to 185° C., particularly from 170 to 180° C., allows the product decomposition to be restricted to a tolerable degree.

This is achieved by applying a sufficiently low vacuum and/or limiting the degree of evaporation of the bottoms and/or minimizing the residence time in the bottom. All alternatives are at first still unsatisfactory since they are expensive in apparatus terms as a result of expensive vacuum generation and enlarged distillation columns or lead to a high product loss and correspondingly reduced product of value yield. The residence time in the bottom can also be shortened advantageously by constructive measures, especially reducing the column diameter in the bottom region (compared to the column part disposed above it), for example by from 25 to 60%. The diameter is selected such that the bottoms level and its possible range of variation, in the event of reduced volume of bottoms, are sufficient to control the bottom effluent and to operate any bottoms circulation pump used. This dimensioning can be carried out by an appropriate person skilled in the art.

One advantage of the side draw column over a conventional distillation column is that it allows a majority of the low boilers formed in the bottoms to be discharged overhead and thus a higher purity of XDA to be achieved. Higher bottom temperatures can thus be allowed than with a "normal" column in which the product is obtained at the top of the column together with the low boilers formed.

The distillation column with side draw is operated under reduced pressure. The pressure in the column bottom (=column top pressure plus pressure drop over the column) is advantageously $\leq 200$ mbar, particularly $\leq 100$ mbar, in particular $\leq 50$ mbar, for example in the range from 30 to 50 mbar.

Advantageously, column internals which have only a low pressure drop in operation are used, in order firstly to minimize the cost and complexity of vacuum generation and secondly to minimize thermal stress on the bottom product. What is crucial for the thermal stress on the bottom product is the bottom temperature, which arises from bottoms concentration and pressure in the column bottom.

The crude XDA used in the process according to the invention has, for example, a purity in the range from 85 to 99.7% by weight, in particular from 90 to 99.5% by weight. The proportion of relatively low boilers, for example benzylamine and corresponding methylbenzylamine, (i.e. 2-, 3- and 4-methylbenzylamine) is preferably in the range from 0.01 to 2% by weight (based in each case on the crude material without ammonia and solvent); the proportion of relatively high boilers, for example amides, amidines, bis-XDAs and higher oligomers, is, for example, in the range from 0.3 to 13% by weight, particularly in the range from 0.5 to 9% by weight.

"Relatively high boilers" are understood to mean components which, under the same conditions, have a higher boiling point than the particular xylylenediamine.

The relatively high boilers are, for example, amides, amidines, bis-XDAs (XDA dimers), and further oligomers, for example of the following formulae: amides: e.g.

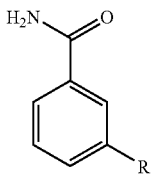

R=—CH$_2$NH$_2$, —CN, —CONH$_2$, —CH$_2$NHCH$_2$-aryl, —C(NH)NCH$_2$-aryl, —CHNCH$_2$-aryl amidines: e.g.

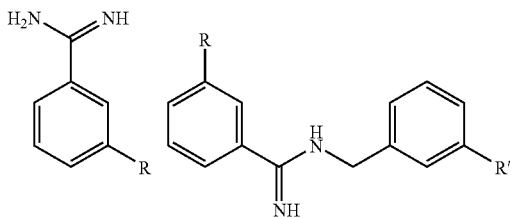

R, R' (each independently)=—CH$_2$NH$_2$, —CN, —CONH$_2$, —CH$_2$NHCH$_2$-aryl, —C(NH)NCH$_2$-aryl, —CHNCH$_2$-aryl
bis-XDAs: e.g. bis-MXDA

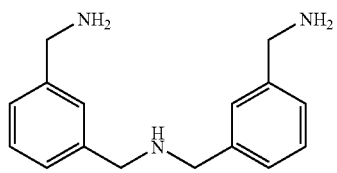

other oligomers: e.g.

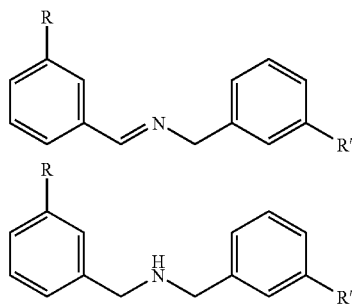

R, R' (each independently)=—CH$_2$NH$_2$, —CN, —CONH$_2$, —CH$_2$NHCH$_2$-aryl, —C(NH)NCH$_2$-aryl, —CHNCH$_2$-aryl.

The bottom effluent is then fed to a further evaporator stage in which an equal or lower vacuum [or else shorter residence time, if appropriate also better vacuum and shorter residence time] is preferably applied than at the top of the distillation column with side draw, and in which the feed stream is evaporatively concentrated as far as possible.

In particular, it is also possible to generate the vacuum for the distillation column with side draw and the downstream evaporation stage with the same vacuum machine, which gives rise to a lower pressure in the downstream evaporation stage than in the bottom of the distillation column, since the pressure drop is greater in the column with side draw owing to the column internals. When the abovementioned points are taken into account, product decomposition is restricted. Since the XDA obtained in the downstream stage is again conducted through the side draw column, the decomposition in the downstream evaporation stage is not crucial for the quality of the XDA, so that it is possible here to balance the substance losses as a result of decomposition and the amount of residue obtained against one another.

The vapors of the downstream evaporation stage are preferably condensed and then fed in liquid form back to the distillation column with side draw. In an alternative variant, vapor compression and vaporous feed to the distillation column is likewise possible. In each case, in a column with vaporous side draw stream, the feed is above the side draw.

In a column with liquid side draw stream, the feed of the crude XDA and the feed of the returned XDA from the evaporation stage are preferably each below the side draw.

The side draw for pure xylylenediamine is preferably arranged as a vaporous side draw stream in the stripping section of the side draw column.

In a particular embodiment, the distillation column with side draw used may advantageously be a dividing wall distillation column with side draw.

In this case, contamination of the xylylenediamine product can be reduced even further by decomposition in the bottoms.

In this case, preference is given to using a liquid side draw stream in the region of the dividing wall. The condensed or compressed vapors of the downstream evaporation stage are preferably added on the feed side (opposite to the side draw side) in the region of the dividing wall.

In the case of a dividing wall column, the addition of the condensed or compressed vapors of the downstream evaporation stage may also be arranged at the same height as or even below the side draw, but in each case preferably in the region of the dividing wall.

The process according to the invention preferably finds use for preparing pure meta-xylylenediamine (MXDA) starting from crude meta-xylylenediamine which has been obtained by hydrogenating isophthalonitrile (IPN) which in turn has been synthesized in particular in a preceding stage by ammoxidation of meta-xylene.

The process according to the invention preferably affords pure XDA having a purity of $\geq$99.9% by weight, in particular $\geq$99.94% by weight.

The pure XDA prepared by the process according to the invention preferably has a residual content of corresponding methylbenzylamine (i.e. 2-, 3- or 4-methylbenzylamine) of $\leq$500 ppm, particularly $\leq$300 ppm, very particularly $\leq$250 ppm, especially $\leq$150 ppm, for example in the range from 5 to 140 ppm.

The process according to the invention preferably affords pure XDA having a distillation yield of $\geq$95%, in particular of $\geq$97%, based in each case on the amount of pure XDA in the crude XDA used.

The process will be illustrated in detail below in a preferred variant with reference to FIG. 1 (in the appendix).

Crude XDA which has been substantially freed of NH$_3$ and, if appropriate, solvents is conducted into the middle region of a side draw column (K100) operated under reduced pressure (stream [1]) and separated there into low boilers (stream [4]), pure XDA (stream [6]) and high boilers (stream

[7]). In the stripping section of the column, a vaporous side draw stream is present, through which pure XDA is drawn off in vaporous form (stream [6]) and then condensed in W101. The bottom heating is preferably effected by means of a steam-heated heat transferer (W 100). The bottom temperature is preferably not more than 180° C. in order to restrict the formation of ammonia and methylbenzylamine from xylylenediamine. The top product [2] is condensed in the heat transferer W 102 and partly returned to the column as reflux (stream [3]). It comprises the low-boiling components, especially methylbenzylamine, but also benzylamine, any solvent present in the crude XDA or residues thereof. For the most part, ammonia is drawn off together with inert gases by means of the vacuum machine (V100) (stream [5]). The bottom product (stream [7]) is fed to a further evaporation stage (W 150). This may, for example, be a thin-film or falling-film evaporator or an otherwise suitable heat transferer. The temperature in W 150 may be higher than in W 100. The temperature is, though, preferably about the same as the temperature in W 150, but evaporation is continued at a lower pressure. Owing to the lower residence time (RT), the decomposition is minimized in the course of concentration. The top product of the evaporator (stream [8]) is condensed in W 151. Inerts and $NH_3$ [11] are drawn off by means of the vacuum machine (V150). The concentrated bottoms (stream [10]) comprise only a little xylylenediamine and are discharged from the process. The condensate (stream [9]) is returned to column K 100 above the side draw. The feed may be above, below or at the same height as the feed of the crude XDA. It is preferably at the same height. When the crude XDA still comprises relatively large amounts of solvent, it may be advisable to arrange the feed of stream [9] below the main feed, but in each case above the side draw.

If the crude XDA only comprises small amounts of low-boiling components, it is also possible to use a column with liquid side draw stream in the rectifying section for purifying distillation of the XDA. The process is then analogous to the above-described process with vaporous side draw stream, except that the feeds for crude XDA and the recycled condensate of the additional evaporation stage are disposed below the liquid side draw stream.

Figure 2:
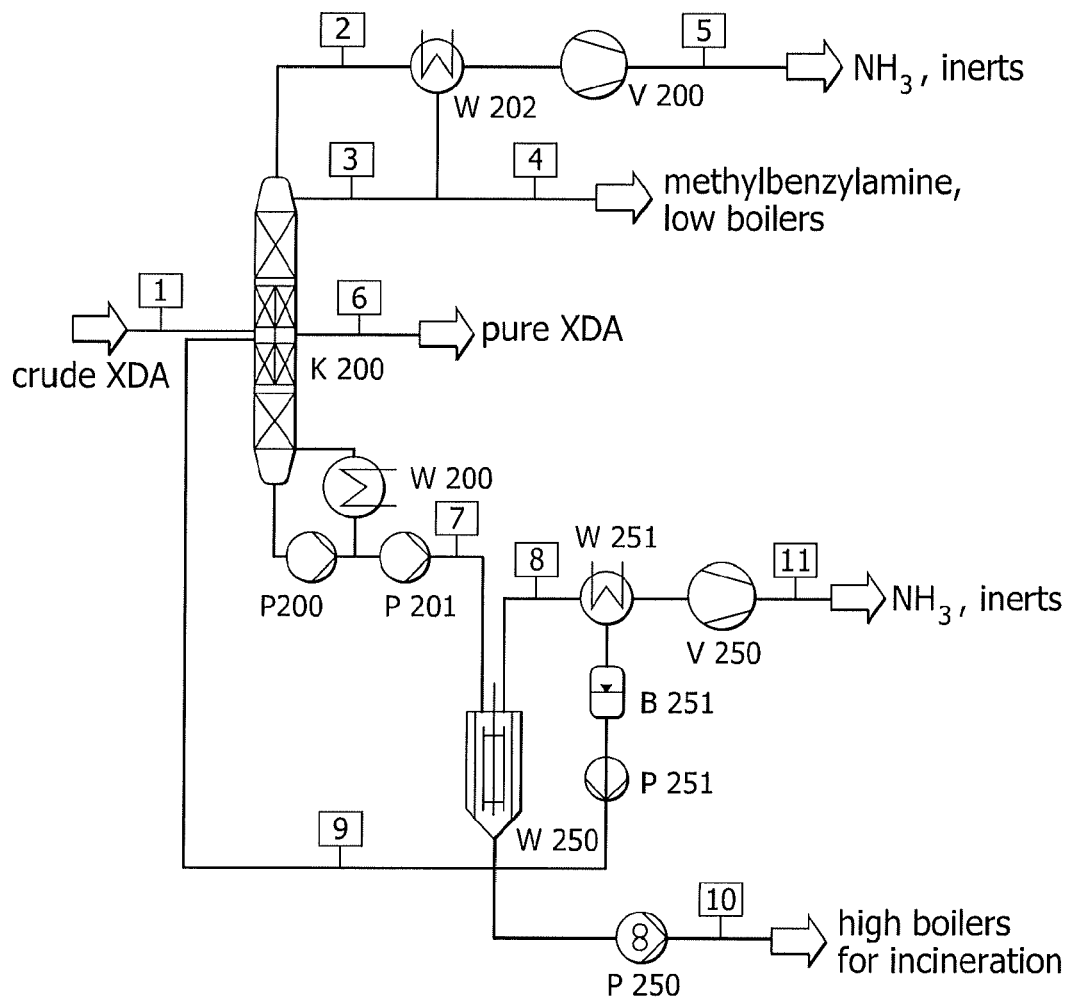
FIG. 2 is a schematic representation of a process in accordance with another embodiment of the present invention.

When a dividing wall column is used instead of a side draw column, the process changes only slightly in a preferred variant: FIG. 2 (in the plant). The dividing wall (the dividing sheet) divides the column into a feed section (side on which the crude XDA feedstream is conducted to the column) and a withdrawal section (side on which the pure XDA side draw stream is conducted out of the column).

With reference to FIG. 2, all reference numerals and designations have identical meanings as used in FIG. 1, but begin with the number "2." For example, K100 in FIG. 1 corresponds to K200 in FIGS. 2, and W100 in FIG. 1 corresponds to W200 in FIG. 2.

The feed of the crude XDA is disposed in the region of the middle of the column, in the region of the dividing wall. The side draw stream of pure XDA may be vaporous, but preference is given to using a liquid side draw stream (stream [6]). The side draw is disposed in the withdrawal side (in FIG. 2, the column section to the right of the dividing wall) in the region of the dividing wall. The recycle stream from the continued evaporation (stream [9]) is returned in the region of the dividing wall on the feed side (in FIG. 2, the column section to the left of the dividing wall), preferably below or at the same height as the feed of the crude XDA stream. Otherwise, the same boundary conditions and apparatus arrangements apply as in the case of use of a side draw column analogously to FIG. 1.

All ppm data in this document are based on the weight.

EXAMPLES

Example 1

Crude MXDA was distilled off in two columns connected in series. In the first column, low boilers were removed via the top (in each case relatively small amounts of water, methylbenzylamine and ammonia). Crude MXDA was drawn off via the bottom and conducted to the second column. In the second column, MXDA was drawn off by means of a vaporous side draw stream in the stripping section, while newly formed low boilers (methylbenzylamine and ammonia) were removed via the top. In the second column, the bottom temperature was 180° C. The purity of MXDA drawn off reached 99.95% (GC area %). The secondary components present were, as well as traces of water and methylated MXDA, in particular 80 ppm of meta-methylbenzylamine (mean value over the entire campaign). In the bottom of the first column in contrast, only less than 10 ppm of meta-methylbenzylamine were detectable, i.e. meta-methylbenzylamine was newly formed in the second column. In the bottom of the second column, an average of approx. 50% by weight of MXDA were present. The distillation yield was 87%.

The example shows that, in a side draw column, it is not possible directly to simultaneously accomplish a certain high purity and a certain high yield.

Example 2

Crude MXDA was distilled in a batchwise distillation apparatus. At top pressure 40 m bar, the last batch, which was obtained at a bottom temperature between 179° C. and 200° C., comprised 0.94% by weight of meta-methylbenzylamine. The remaining bottom product still comprised 59.4% by weight of MXDA. The bottom product was concentrated further in a thin-film evaporator and was still highly free-flowing even at MXDA content 10% by weight. Owing to the high bottom temperature, the top product comprised approx. 1% by weight of meta-methylbenzylamine. After another distillation, on-spec (>99.9% by weight of MXDA and meta-methylbenzylamine ~100 ppm) MXDA was obtained therefrom.

The example shows how greatly product decomposition rises at higher temperature. The example also shows that the bottom product can be concentrated very greatly and is then still industrially easy to handle. The example also shows that the top product of the bottoms extraction, which has a high content of methylbenzylamine, can be distilled again and MXDA can be obtained therefrom in high purity. The example thus shows the inventive concentration of the bottoms, the collection of the (insufficiently pure) distillate and the recycling to the distillation, as a result of which the distillation yield is increased. Only a very small amount of MXDA is lost with the concentrated bottom product and by decomposition.

What is claimed is:
1. A process comprising:
continuously distilling a crude xylylenediamine in a column to form a pure xylylenediamine and a bottom product, wherein the column comprises a distillation column having a side draw and the distillation column is operated under a reduced pressure and a bottom temperature of 185° C. or less,
drawing off the pure xylylenediamine from the side draw,
evaporatively concentrating the bottom product of the distillation column in an additional evaporation stage to form a condensate, and
returning the condensate into the distillation column.

2. The process according to claim 1, wherein the pure xylylenediamine is drawn off as a vaporous side draw stream from the side draw in a stripping section of the distillation column.

3. The process according to claim 1, wherein the condensate is returned into the distillation column above the side draw.

4. The process according to claim 1, wherein the distillation column with side draw comprises a dividing wall distillation column.

5. The process according to claim 4, wherein the pure xylylenediamine is drawn off as a liquid side draw stream in the region of the dividing wall.

6. The process according to claim 4, wherein the condensate is returned into the distillation column in the region of the dividing wall on the feed side.

7. The process according to claim 1, wherein the crude xylylenediamine comprises meta-xylylenediamine.

8. The process according to claim 1, wherein the crude xylylenediamine has a purity of 85 to 99.7% by weight.

9. The process according to claim 1, wherein the distillation column with side draw is operated at a bottom pressure of 200 mbar or lower.

10. The process according to claim 1, wherein the distillation column with side draw is operated at a bottom pressure of 100 mbar or lower.

11. The process according to claim 1, wherein the distillation column with side draw is operated at a bottom pressure of 50 mbar or lower.

12. The process according to claim 1, wherein the additional evaporation stage is operated at the same pressure as or a lower pressure than the top pressure of the distillation column with side draw.

13. The process according to claim 1, wherein the pure xylylenediamine a purity of $\geqq 99.9\%$ by weight.

14. The process according to claim 1, wherein the pure xylylenediamine comprises ortho-xylylenediamine having a residual content of 2-methylbenzylamine of $\leqq 500$ ppm by weight.

15. The process according to claim 1, wherein the pure xylylenediamine comprises meta-xylylenediamine having a residual content of 3-methylbenzylamine of $\leqq 500$ ppm by weight.

16. The process according to claim 1, wherein the pure xylylenediamine comprises para-xylylenediamine having a residual content of 4-methylbenzylamine of $\leqq 500$ ppm by weight.

17. The process according to claim 1, wherein the distillation column with side draw has a diameter reduced in a bottom region compared to a diameter of the column in a region disposed above the bottom region.

* * * * *